US012605515B1

(12) United States Patent (10) Patent No.: US 12,605,515 B1
Gravett et al. (45) Date of Patent: Apr. 21, 2026

(54) AEROSOL DELIVERY DEVICE WITH COMPLETED DOSAGE INDICATOR

(71) Applicant: Trudell Medical International Inc., London (CA)

(72) Inventors: Matthew Gravett, London (CA); Daniela Manotas, London (CA); Hannah Hammond, Hamilton (CA); Robert Frank Costa, London (CA)

(73) Assignee: Trudell Medical International Inc., London (CA)

( * ) Notice: Subject to any disclaimer, the term of this patent is extended or adjusted under 35 U.S.C. 154(b) by 712 days.

(21) Appl. No.: 18/063,237

(22) Filed: Dec. 8, 2022

Related U.S. Application Data

(60) Provisional application No. 63/288,198, filed on Dec. 10, 2021.

(51) Int. Cl.
*A61M 15/00* (2006.01)
*A61M 16/20* (2006.01)

(52) U.S. Cl.
CPC ...... *A61M 15/008* (2014.02); *A61M 15/0086* (2013.01); *A61M 16/208* (2013.01); *A61M 2205/581* (2013.01)

(58) Field of Classification Search
CPC ........ A61M 15/00–085; A61M 16/208; A61M 2205/581; A63B 23/18–185
See application file for complete search history.

(56) References Cited

U.S. PATENT DOCUMENTS

| | | | | |
|---|---|---|---|---|
| 5,522,380 | A | * 6/1996 | Dwork | A61M 15/0003 |
| | | | | 128/200.23 |
| 5,839,430 | A | * 11/1998 | Cama | A61B 5/411 |
| | | | | 128/200.14 |
| 6,073,628 | A | 6/2000 | Butler et al. | |
| 8,464,706 | B2 | 6/2013 | Crockford et al. | |
| 8,550,067 | B2 | 10/2013 | Bruce et al. | |
| 8,820,316 | B2 | 9/2014 | Crockford et al. | |
| 2015/0265874 | A1* | 9/2015 | Rettig, Jr. | A61B 5/0875 |
| | | | | 600/538 |

(Continued)

FOREIGN PATENT DOCUMENTS

EP          1 201 258          5/2022

OTHER PUBLICATIONS

Medgadget, "Watchhaler to Turn Inhalation Into Child's Play", Jul. 17, 2008, https://www.medgadget.com/2008/07/watchhaler_to_turn_ inhalation_into_childs_play.html (2 pages).

*Primary Examiner* — Bradley H Philips
*Assistant Examiner* — Kira B Daher
(74) *Attorney, Agent, or Firm* — Crowell & Moring LLP

(57) ABSTRACT

A medication delivery system includes a chamber housing defining an interior volume. The chamber housing has an inlet adapted to receive a dosage of medicament and an outlet spaced apart from the inlet. The inlet and outlet are in fluid communication with the interior volume. A flow channel is in fluid communication with the interior volume. A dosage indicator is translatable in the flow channel from a pre-inhalation position to a complete dosage position, wherein a positioning of the dosage indicator in the complete dosage position indicates a complete administration of the dosage of medicament through the outlet. Methods of using and assembling the system are also provided.

24 Claims, 9 Drawing Sheets

FIG. 5

(56)  References Cited

U.S. PATENT DOCUMENTS

2017/0333645  A1     11/2017  Alizoti et al.
2019/0059811  A1 *   2/2019   Dashiell ................. A61M 11/00
2019/0366018  A1     12/2019  Conlon et al.
2020/0390988  A1 *   12/2020  Lim  .................. A61M 15/0088
2021/0045657  A1 *   2/2021   Thomas  ............... A61B 5/0022

* cited by examiner

AEROSOL DELIVERY DEVICE WITH COMPLETED DOSAGE INDICATOR

This application claims the benefit of U.S. Provisional Application No. 63/288,198, filed Dec. 10, 2021 and entitled "Aerosol Delivery Device With Completed Dosage Indicator," the entire disclosure of which is hereby incorporated herein by reference.

TECHNICAL FIELD

The present invention relates generally to an aerosol delivery device, such as a holding chamber, which is configured to provide indicia when the user has completed the inhalation of a predetermined volume, or completed the inhalation of a prescribed dosage of medicament, together with methods of delivering aerosol medicament and indicating the complete inhalation of the dosage of the medicament and methods of assembling the delivery device.

BACKGROUND

The use of an aerosol medication delivery apparatus and system to administer medication in aerosol form to a patient's lungs by inhalation (hereinafter "aerosol delivery system(s)") is well known in the art. Such devices and systems include for example pressurized metered-dose inhalers (pMDIs), pMDI add-on devices, such as holding chambers, devices including a chamber housing and integrated actuator suited for a pMDI canister, nebulizers, dry powder inhalers and other such devices. While some aerosol delivery systems are configured to provide a visual indication to alert a caregiver when a patient is inhaling, such systems typically do not alert the user or caregiver that the user has inhaled all of their medication.

SUMMARY

In one aspect, one embodiment of a medication delivery system includes a chamber housing defining an interior volume. The chamber housing has an inlet adapted to receive a dosage of medicament and an outlet spaced apart from the inlet. The inlet and outlet are in fluid communication with the interior volume. A flow channel is in fluid communication with the interior volume. A dosage indicator is translatable in the flow channel from a pre-inhalation position to a complete dosage position, wherein a positioning of the dosage indicator in the complete dosage position indicates a complete administration of the dosage of medicament through the outlet. In one embodiment, the dosage indicator is visible through the flow channel as the dosage indicator is translated between the pre-inhalation position and the complete dosage position.

In yet another aspect, a medication delivery system includes a chamber housing defining an interior volume and having an inlet adapted to receive a dosage of medicament and a user interface spaced apart from the inlet in a longitudinal direction. The inlet and user interface are in fluid communication with the interior volume. A flow channel is in fluid communication with the interior volume and extends in the longitudinal direction. A dosage indicator is translatable in the flow channel from a pre-inhalation position proximate the user interface to a complete dosage position proximate the inlet. A positioning of the dosage indicator in the complete dosage position indicates a complete administration of the dosage of medicament through the user interface. The dosage indicator includes a turbine that is rotatable in the flow channel as the dosage indicator is translated between the pre-inhalation position and the complete dosage position. In various embodiments, the dosage indicator is observable in the flow channel, for example the dosage indicator may be visible or audibly recognized as it moves in the flow channel and reaches the complete dosage position.

In another aspect, one embodiment of a method of delivering an aerosolized medication includes disposing an aerosolized dose of medicament in an interior volume of a chamber housing, inhaling through a user interface coupled to a chamber housing and thereby withdrawing the aerosolized dose of medicament from the interior volume, translating a dosage indicator in a flow channel in fluid communication with the chamber housing from a pre-inhalation position to a complete dosage position, observing the translation of the dosage indicator, and ceasing inhaling when the dosage indicator reaches the complete dosage position. In one embodiment, the dosage indicator is rotated as it is translated from the pre-inhalation position to the complete dosage position.

The various aspects and embodiments provide significant advantages over other medication delivery systems and methods. For example, and without limitation, the movement of the dose indicator allows users and caregivers to visually and/or audibly detect when the user has inhaled all of their medications. This feedback system may be particularly well suited for caregivers and users that may not be able to generate enough inhalation volume to inhale a complete dosage of medicament in one breath. The dosage indicator provides indicia to the user once the entirety of a predetermined, prescribed dosage of medicament has been inhaled, as opposed to prior devices that may only provide indicia that an inhalation flow is occurring, rather than indicating how much they have inhaled. Moreover, the dosage indicator is observable (e.g., visible and/or audible) to both the user and the caregiver in one embodiment.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

DETAILED DESCRIPTION OF THE DRAWINGS AND PRESENTLY PREFERRED EMBODIMENTS

Figures 1, 2:
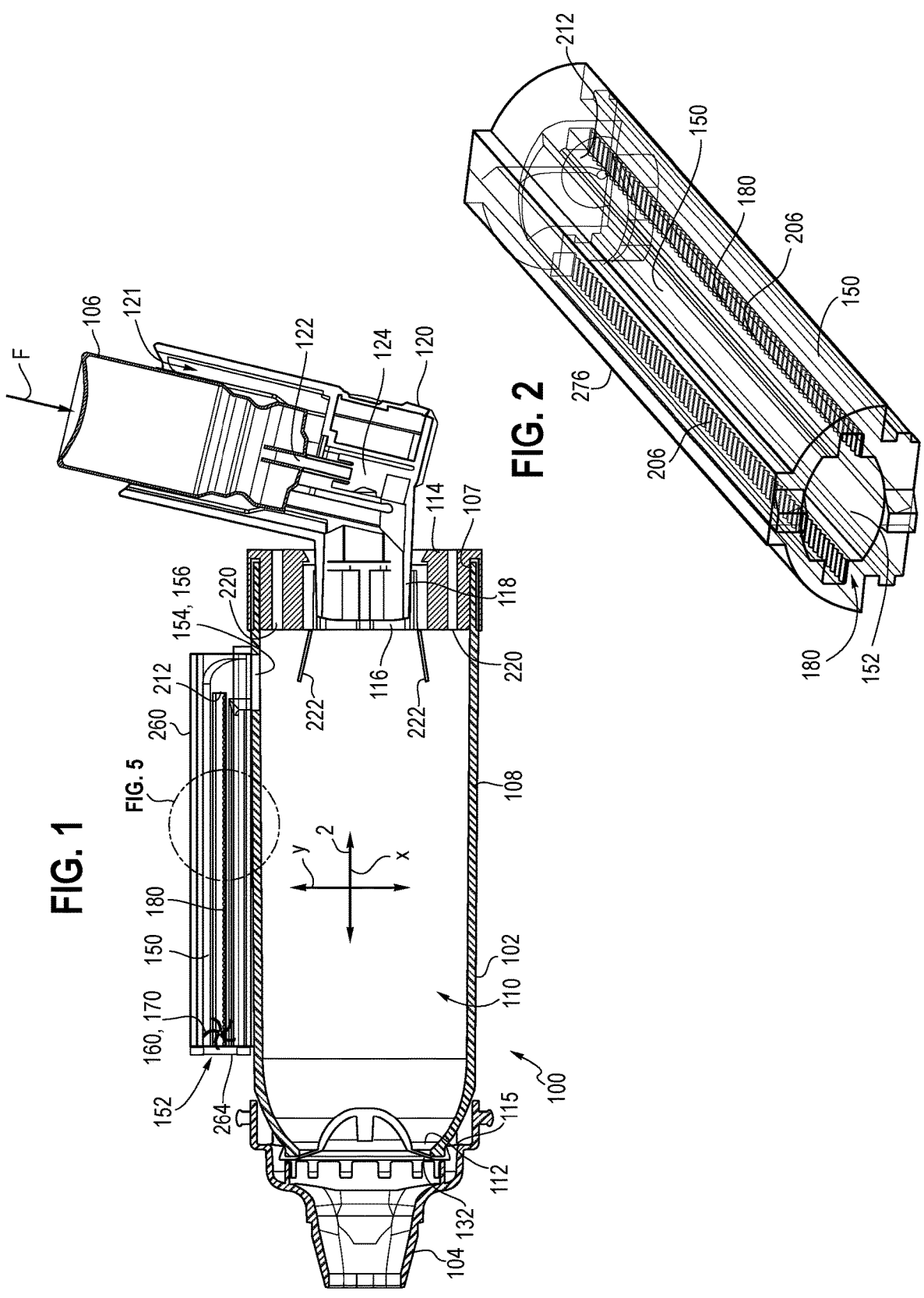
FIG. 1 is a side, cross-sectional view of one embodiment of a medicament delivery system configured with a completed dosage indicator.
FIG. 2 is a perspective view of a flow channel.
Figures 3, 4A, 4B, 5:
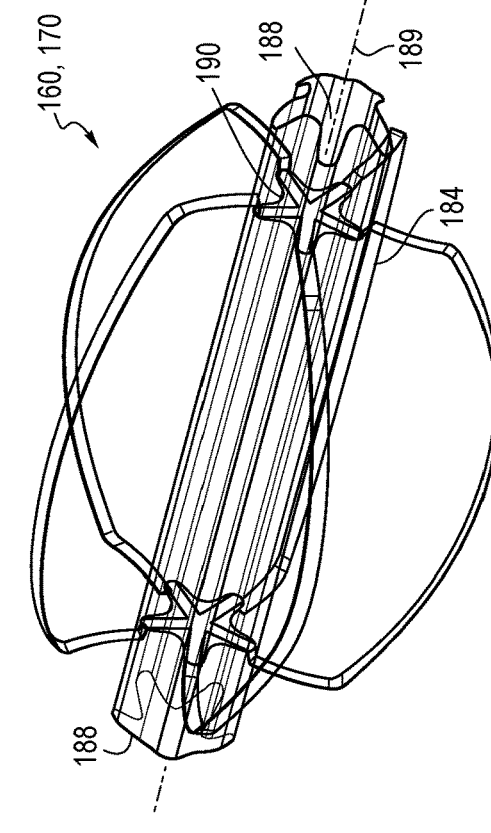
FIG. 3 is a front, perspective view of a backpiece adapter.
FIG. 4A is a front view of one embodiment of a turbine.
FIG. 4B is a perspective view of the turbine shown in FIG. 4A.
FIG. 5 is an enlarged partial, cross-sectional view of the flow channel including a track.
Figure 6:
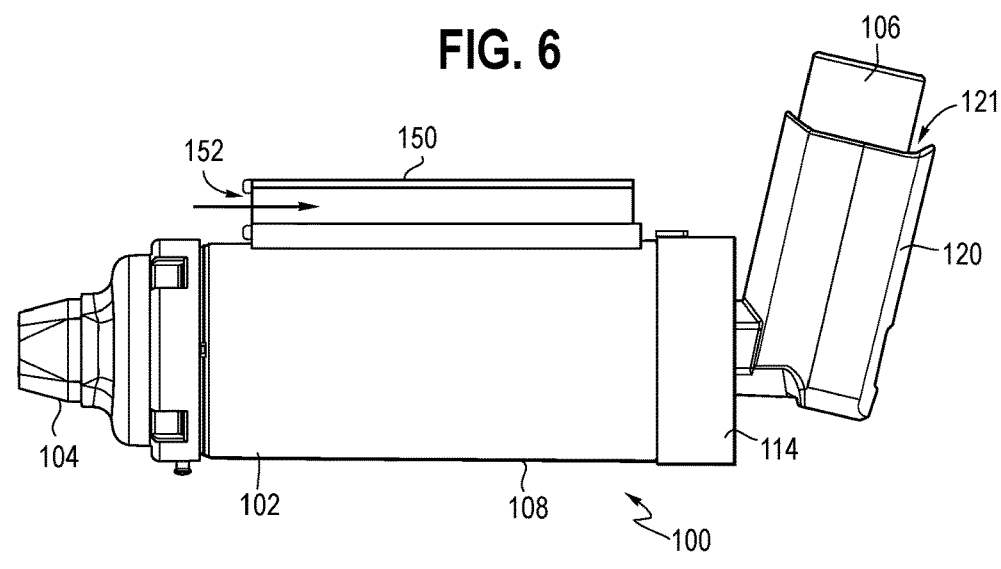
FIG. 6 is a side view of the medicament delivery system shown in FIG. 1.

It should be understood that the term "plurality," as used herein, means two or more. The terms "longitudinal" as used herein means of or relating to length or the longitudinal direction 2, for example between the opposite ends of the holding chamber or flow channel. The terms "lateral" and "transverse" as used herein, means situated on, directed toward or running from side to side (front and back of a worksurface), and refers to a lateral direction 4 orthogonal to the longitudinal direction. For example, the X direction may correspond to the longitudinal direction, which is horizontal when the device is in a use position, the Y direction may extend in a vertical direction when the device is in a use position, and the Z direction may correspond to the lateral direction, which is also horizontal when the device is in the use position. The term "direction" corresponds to an axis or line, rather than a vector. The term "coupled" means connected to or engaged with whether directly or indirectly, for example with an intervening member, and does not require the engagement to be fixed or permanent, although it may be fixed or permanent (or integral), and includes both mechanical and electrical connection. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. For example, a "first" side may be later referred to as a "second" side depending on the order in which they are referred. It should also be understood that designation of "first" and "second" does not necessarily mean that the two features, components or values so designated are different, meaning for example a first side may be the same as a second side, with each simply being applicable to separate but identical components. As used herein: the term "substance" includes, but is not limited to, any substance that has a therapeutic benefit, including, without limitation, any medication; the terms "user" and "patient" includes humans and animals; and the term "aerosol delivery devices or system(s)" includes pressurized metered-dose inhalers (pMDIs), pMDI add-on devices, such as holding chambers, devices including a chamber housing and integrated actuator suited for a pMDI canister, nebulizers and dry powder inhalers.

FIGS. 1, 6 and 8A-C show an embodiment of an aerosol delivery system 100. The system 100 includes a holding chamber 102 or conduit, an interface 104, an inhalation valve 132 and a source of a substance, such as a pMDI canister, attached to a rear end 107 of the holding chamber 102. The holding chamber 102 includes a chamber housing 108 that has a generally cylindrical cross-sectional shape that defines an interior volume 110 of space for receipt therein of aerosolized medication from the inhaler 106, e.g., pMDI. A front end of the chamber housing 108 includes an outlet 112, configured in one embodiment as an opening that is in fluid communication with the interior volume 110 of space of the chamber housing 108. The outlet 112 defines the periphery of a flow path as it exits the opening. The interface 104 may be configured as a mouthpiece, mask (nasal or oral/nasal), tube, or other suitable user interface, which is in fluid communication with the outlet/opening 112. The inhalation valve 132 may be disposed over the opening to provide for one-way flow through the opening during inhalation but prevents back flow into the interior volume 110 during exhalation. An exhalation valve 115 may be provided to allow for one-way flow to the ambient environment surrounding the system 100 during exhalation, but prevents air entrainment through an exhalation opening during inhalation. A rear end 107 of the chamber housing 108 is attached to a detachable and flexible backpiece 114, or adapter, that includes an inlet 116, configured in one embodiment as an opening suited to receive the mouthpiece portion 118 of the pMDI receptacle 120, otherwise referred to as an actuator boot, that houses the pMDI canister. The canister includes a valve stem 122 disposed in a well 124 in the bottom of the receptacle 120. The inlet 116 is in fluid communication with the interior volume 110. Examples of possible pMDI adapters and canisters to be used in conjunction with the holding chamber 102 are also described in U.S. Pat. Nos. 5,012,803, 5,012,804, 5,848,588 and 6,293,279, the entire contents of each of which is incorporated herein by reference. It should be understood that other aerosol delivery systems may have various one or more interior volumes fillable with an aerosolized medicament, with one or more outlets and one or more inlets communicating with the interior volume, including devices having a chamber housing and integrated actuator suited for a pMDI canister, nebulizers, dry powder inhalers and other such devices. The holding chamber 102 extends in the longitudinal direction 2, with the inlet 116 and outlet 112 being longitudinally spaced.

In one embodiment, a force F may be applied to the canister, thereby moving the valve stem 122 of the pMDI canister to discharge a predetermined dosage of medicament from the discharge end, e.g., mouthpiece portion 118, of the pMDI receptacle in aerosol form into the interior volume 110 of the chamber housing 108. The aerosol medication particles within the interior volume 110 and chamber housing 108 are thereafter withdrawn through the outlet 112 by having the user/patient inhale through the interface 104.

The pMDI canister contains a substance, preferably a medication suspension or solution under pressure. For example, the substance dispensed may be an HFA propelled medication suspension or solution formulation. Other medicaments, or medications, and propellants, such as CFC may also be used. It should be pointed out that while the described embodiments regard an aerosol delivery system for the delivery of an aerosolized medication from a pMDI, other aerosol delivery systems are contemplated that can be used within the spirit of the present invention. For example, it is contemplated that the completed dosage indicator may be incorporated with an aerosol delivery system such as existing ventilator systems, dry powder inhalers and nebulizers, in a manner similar to that described below. Examples of nebulizers that can be adapted to include such an indicator are disclosed in U.S. Pat. Nos. 5,823,179 and 6,044,841, the entire contents of which are incorporated herein by reference.

The present invention is not limited to the treatment of human patients. For example, it is contemplated that the complete dosage indicator may be incorporated in a mask for administering medication to animals, including for example and without limitation equines, cats, dogs, etc.

Figure 10:
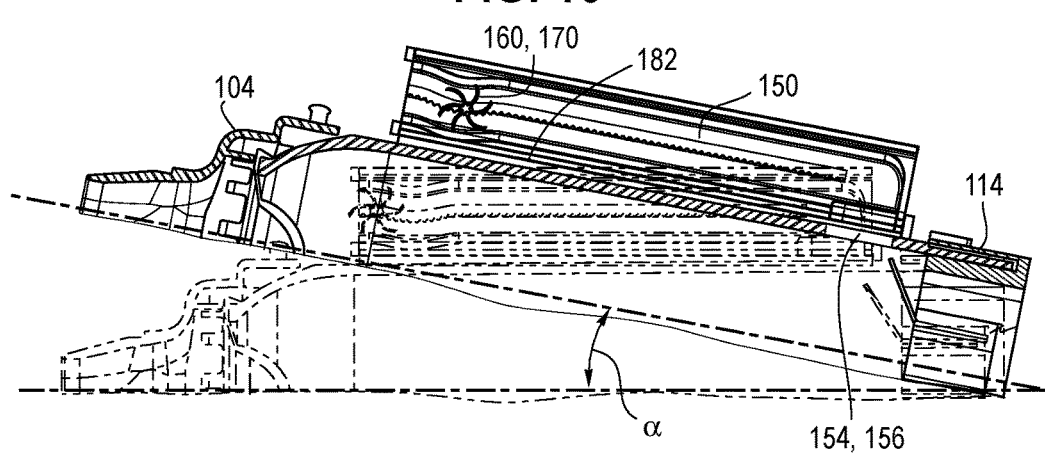
FIG. 10 is a cross-sectional view of one embodiment of a medicament delivery device moving from a horizontal, use position to a tilted position.
Figure 11:
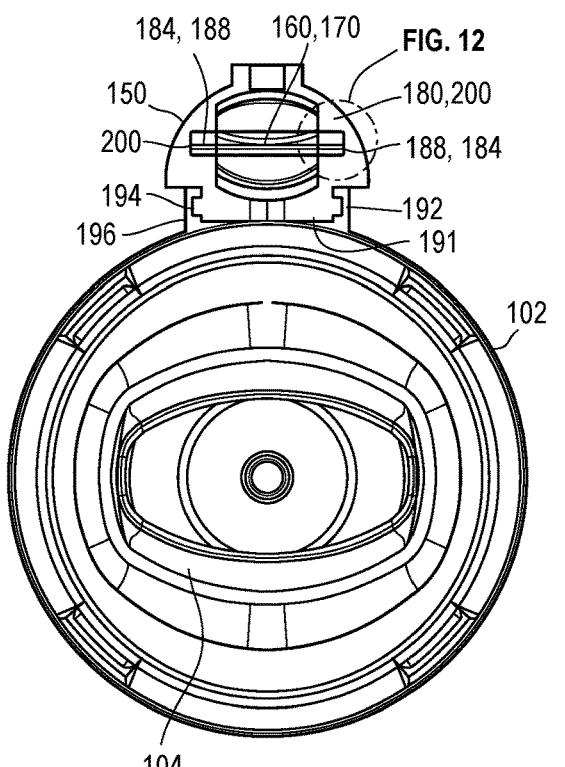
FIG. 11 is an end view of one embodiment of a medicament delivery device.

Referring to FIGS. 1, 5-11 and 17-22, the aerosol delivery system 100, otherwise referred to as an aerosol delivery device, is configured with a flow channel 150 and a dosage indicator 160, configured as a turbine 170 in one embodiment. In one embodiment, the flow channel 150 is configured as a tube or long tube-like structure mounted lengthwise on, or extending in a longitudinal direction 2 along, a side of the holding chamber 102, for example a top thereof, such that the flow channel is visible to the user 148 engaged with the interface, or a nearby caregiver. As shown in FIG. 11, the flow channel has a pair of laterally spaced insert portions 192, or flanges, extending laterally outwardly from a central base 191. The insert portions are received in a pair of channels/slots 194 formed in a guide 196 disposed on top of the holding chamber. The guide 196 may be integrally formed with the holding chamber 102. The flow channel 150 is coupled to the holding chamber by sliding the insert portions 192 into the slots 194 until the flow channel is in fluid communication with the interior volume. In other embodiments, the flow channel may be integrally formed with the holding chamber as a one-piece component. The flow channel 150, or tube, may be transparent such that the user, or caregiver, is able to see into the interior of the flow channel. The flow channel 150, or interior space thereof, is in fluid communication with the interior volume 110 of the holding chamber when installed. In one embodiment, the flow channel has an inlet 152, or opening, and an outlet 154, or opening, which is in fluid communication with and defines an inlet 156 for the interior volume. The outlet 154 communicates with the holding chamber 102 close to the backpiece 114, or inhaler adaptor (distal), while the inlet 152 is positioned close to the interface 104 (e.g., mouthpiece/mask) and is in direct fluid communication with the ambient air surrounding the system 100. In another embodiment, the flow channel may have an outlet in direct fluid communication with the user interface, rather than the interior volume of the holding chamber.

Figure 7A:
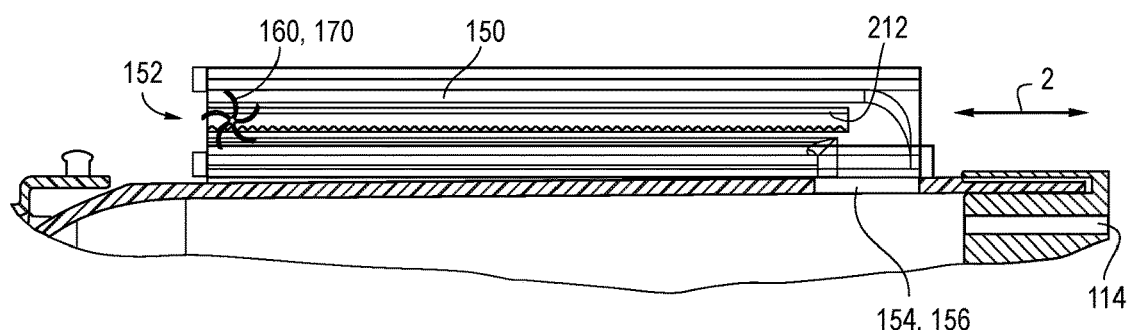
FIGS. 7A-7C are cross-sectional views of the flow channel with a dose indicator being translated from a pre-inhalation position to a completed dose position.
Figure 7B:
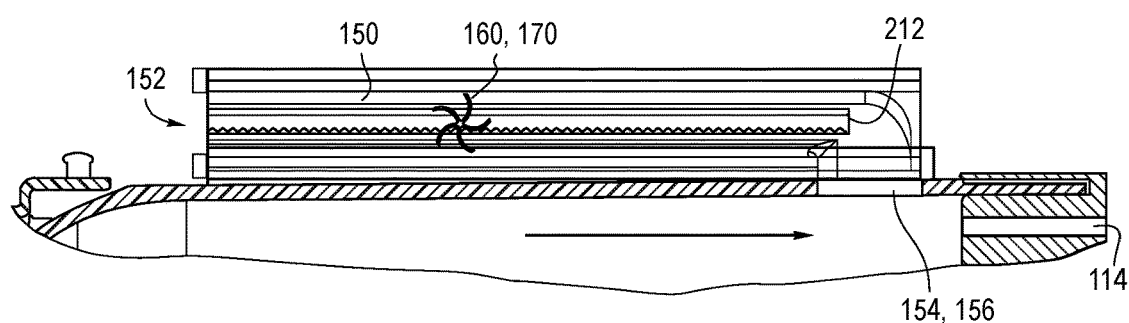
Figure 7C:
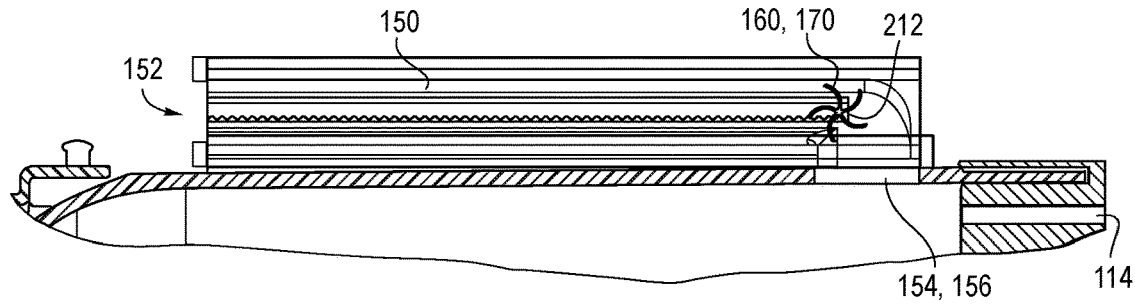
Figure 8A:
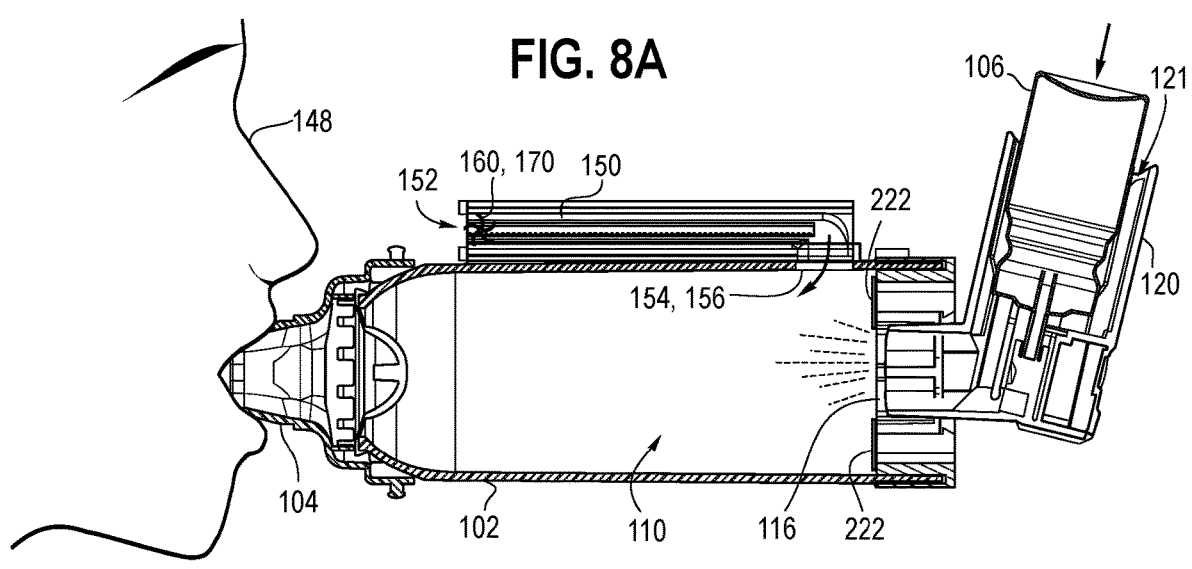
FIGS. 8A-8C are cross-sectional views of a medicament delivery system with a variable size opening providing three different inlet sizes responsive to different inhaler resistances.
Figure 8B:
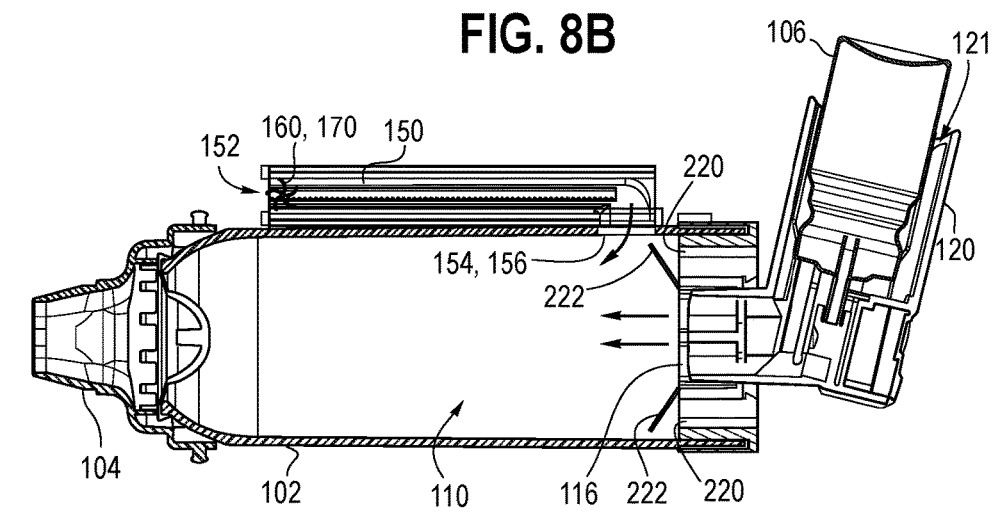
Figure 8C:
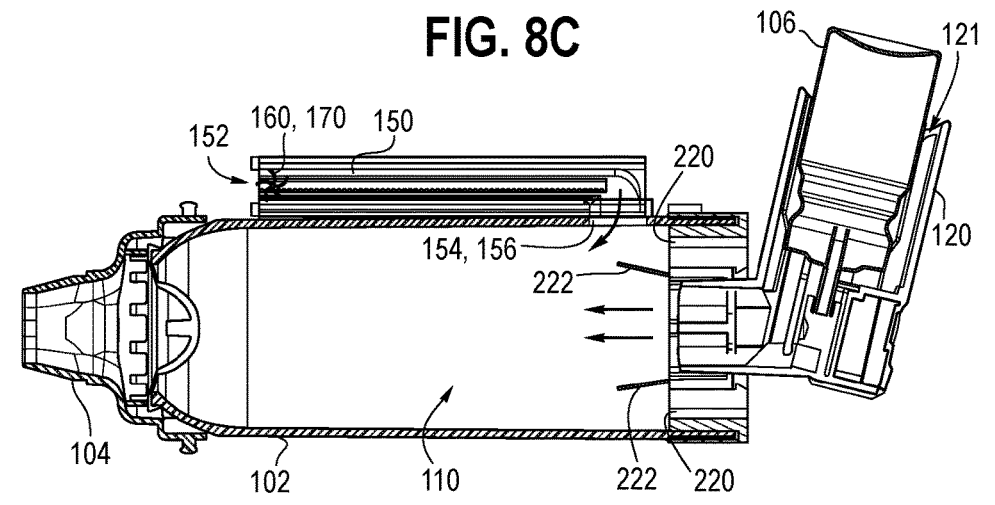

The dosage indicator 160 is moveable in the flow channel 150 in the longitudinal direction 2 from a pre-inhalation position to a complete dosage position. In one embodiment, the dosage indicator 160 is translatable and rotatable in the flow channel 150 from the pre-inhalation position to the complete dosage position. The phrase "pre-inhalation position" refers to the position of the dosage indicator immediately preceding inhalation by the user through the aerosol delivery device, as shown for example in FIG. 7A. The phrase "complete dosage position" refers to the position of the dosage indicator after a predetermined, or prescribed, dosage of medicament, aerosolized in the holding chamber, has been administered, for example through inhalation and deposition of the medicament in the lungs of the user. In other words, positioning of the dosage indicator in the complete dosage position indicates to the user and caregiver that a complete administration of the dosage of medicament through the outlet has been accomplished, regardless of how many inhalation sequences have occurred (e.g., one or more). In one embodiment, as shown in FIG. 7C, the dosage indicator is in the complete dosage position. The term "translatable" refers to the displacement or movement of a component a certain distance in space defined by the X, Y and/or Z axis, such that the component, in the absence of rotation, has a different X, Y and/or Z coordinate after being translated. For example, the dosage indicator may be translated only in the X direction. It should be understood that the component may additionally be rotated about any of the X, Y and/or Z axis before, during and/or after being "translated." The component may be translated by sliding, rolling or other types of movement. In this way, a component such as the dosage indicator may be simultaneously translated (moved a distance in space from a first position to a second position) and rotated as it is translated between the first and second position. In one embodiment, the dosage indicator 160 is visible through and in the flow channel 150, which may be transparent, or see-through, and made out of a transparent material, as the dosage indicator 160 is translated and rotated between the pre-inhalation position and the complete dosage position. It should be understood that in other embodiments, the dosage indicator is only translated, e.g., through sliding, between the pre-inhalation position and complete dosage position.

For example, in one embodiment, the turbine 170 is rotatable as the turbine is translated from the pre-inhalation position to the complete dosage position. In one embodiment, the dosage indicator 160 is translatable along a linear path between the pre-inhalation position and the complete dosage position. The term "linear" refers to movement along a straight line. In other embodiments, the dosage indicator 160 is translatable along a planar path between the pre-inhalation position and the complete dosage position, meaning the dosage indicator moves within a plane defined by two axes (e.g., X and Y), but may also be rotated about an axis (Z) normal to the plane. In one embodiment, the dosage indicator 160 is closer to the user interface 104 in the pre-inhalation position than in the complete dosage position, meaning the dosage indicator travels away from the user 148 during the inhalation sequence. In other embodiments, the relative positioning may be reversed, with the dosage indicator being further from the user interface in the pre-inhalation position than in the complete dosage position, meaning the dosage indicator travels toward from the user during the inhalation sequence.

Figure 9:
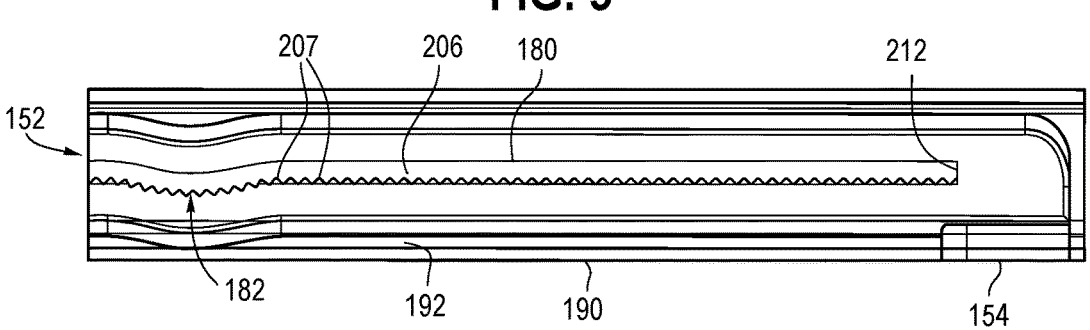
FIG. 9 is a cross-sectional view of an alternative embodiment of a flow channel and track.

In one embodiment, the flow channel 150 comprises a track 180, wherein the dosage indicator is moveable along the track between the pre-inhalation position and the complete dosage position. The dosage indicator may slide (translate) or roll (translate and rotate) along the track. As shown in FIGS. 9 and 10, the track 180 may be configured with a dip 182 adjacent the dosage indicator when positioned in the pre-inhalation position. The interface between the dosage indicator 160 and track 180 may provide an auditory indicator adapted to provide an audible signal when the dosage indicator is translated to the complete dosage position.

Referring to FIGS. 1, 4A-B, 7A-C and 13-16, the turbine 170 includes a shaft 184 and some branching fin blades 186 that produce drag and extend radially from the shaft 184, causing the turbine to spin or rotate about the shaft 184 when exposed to an air flow. In one embodiment, the shaft 184 extends laterally outwardly in the Z direction past the lateral width of the blade/fins 186 on both sides thereof, with at least a portion of the shaft configured as a pinion gear 188 having a plurality of circumferentially spaced teeth 198. The fin blades 186 may be curved, or planar. In one embodiment, the teeth 198 are aligned with the blades 186, as shown for example in FIGS. 4A and 14.

In one embodiment, the flow channel includes a pair of laterally spaced tracks 180, each defined by a longitudinally extending slot or channel 200. In one embodiment, each track has an upper and lower surface 202, 204 defining the channel, as shown for example in FIG. 12. One or both of the upper and lower surfaces may include, or be configured as, a rack 206. The racks may be linear, or be disposed within a plane, and are configured with a plurality of teeth 207. The turbine 170 is disposed or positioned in the interior space of the flow channel 150, with the pinion gears 188 disposed on and engaging the racks embedded in the slots on the sides of the channel. The ends 208 of the shaft are spaced apart from a side wall 210 of the channel 200, providing clearance such that the shaft ends 208 do not bind on the wall 210 and create undue friction wherein the turbine 170 may roll freely (translate and rotate) through the flow channel 150. In one embodiment, the gap between the ends 208 of the shaft and the side wall 210 is no less than 0.05 mm and no more than 3 mm. In one embodiment, the gap is 0.5 mm.

When the user 148 inhales through the user interface 104, such as the mouthpiece or mask, the aerosolized medication and air mixture disposed in the interior volume 110 of the holding chamber 102 is pulled through the inhalation valve 132, as air backfills/refills the holding chamber. In one embodiment, the air that re-fills the holding chamber 102 comes from the ambient environment through two or more inlets. In one embodiment, the backfilling air may come from three sources: through the inhaler 106 and inlet 116 (pMDIs and SMIs), through the inlet 156 communicating with the flow channel 150 and through one or more inlets 220 in the MDI adapter (e.g., backpiece 114), which are spaced apart from the inlet 116. As air is pulled through the flow channel 150, the turbine 170 will begin to move from the pre-inhalation position, wherein the turbine is positioned at proximal end of the holding chamber, towards the distal end. The user's inhalation rate over time will cause the turbine 170 to hit a stop 212 at or near an end of the flow channel 150, which defines the complete dosage position, when the patient has inhaled enough volume to ensure that the patient has emptied the interior volume of the chamber of medicament. The volume may vary by age group, for example, and may be, or approximately be, 500 mL for adults, 300 ml for children and 150 mL for infants. To reset the dosage indicator 160 for the next use, the user simply tilts the holding chamber 102 (e.g., counterclockwise when viewed as shown in FIG. 1, such that the turbine 170 rolls back to the proximal, pre-inhalation position.

There are a wide variety of inhaler 106 and receptacle 120 configurations, and therefore a wide variety of inhaler flow resistances, which are dependent on the geometry of the inhaler and receptacle air passage 121. In one embodiment, if ambient air backfilling the interior volume 110 during inhalation enters the chamber only through first and second inlets 116, 156, defined for example by the mouthpiece portion 118 disposed in the inlet 116 and the inlet 156 communicating with the flow channel 150, the difference in resistance between different inhalers/receptacles may cause the airflow through the flow channel 150 to change depending on what inhaler/receptacle is used, and therefore resulting in different travel speeds of the turbine 170. For example, an inhaler/receptacle combination with higher resistance will promote more airflow through the flow channel 150, which has a lower resistance. Conversely, if an inhaler/receptacle has a low resistance, more air will pass through the inhaler/receptacle compared to the flow channel 150, which may have a relatively higher resistance, therefore resulting in different inhalation volume responses from the turbine 170. In one embodiment, the turbine 170 is calibrated to a median resistance across all types of inhalers/receptacles that would be used with the aerosol delivery device, or the turbine 170 may be calibrated to the highest resistance inhaler/receptacle, with the dosage indicator reaching the complete dosage position for the lowest resistance inhaler.

Figure 24:
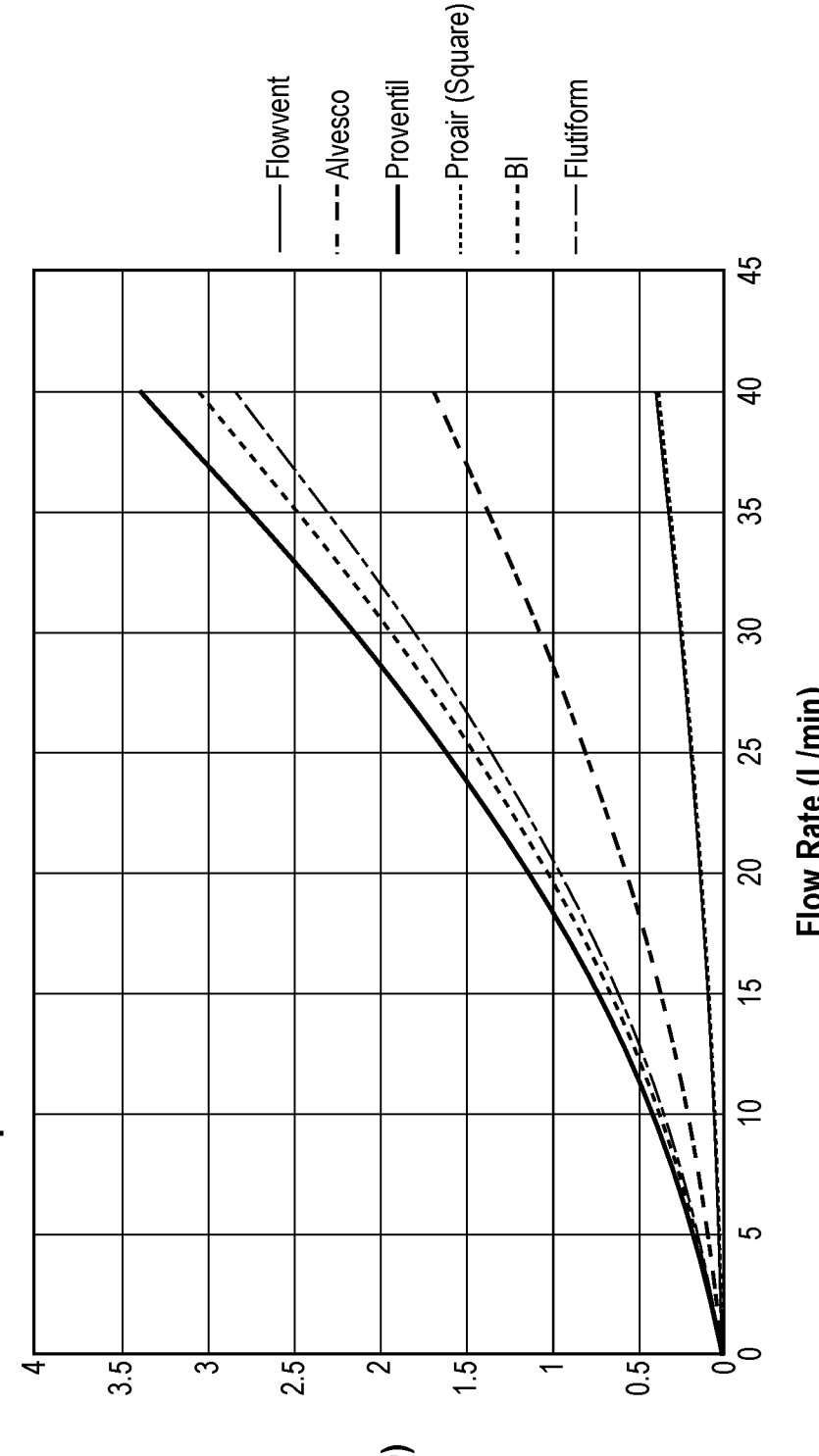
FIG. 24 is a graph of pMDI resistance v. flow rate for different types of inhalers.

In an alternative embodiment, one or more third inlets 220 are provided in fluid communication with the interior volume 110. In one embodiment, a pair of inlets 220 are provided in the backpiece 114, with each inlet 220 each having a variable size opening. In one embodiment, a one-way, variable, valve 222 is disposed over the inlet. The inlet 220 and valve 222 may be incorporated directly into the holding chamber, or the inlet and valve may be incorporated into the backpiece 114, otherwise referred to as an adapter, as shown for example in FIGS. 1 and 3. The valve 222 is designed to open when the inhalation resistance through the inhaler/receptacle is high, and to remain closed when the resistance is low. Referring to FIG. 24, the valve 222 is tuned to remain closed for the lowest resistance inhalers such as Pro-Air HFA inhalers with built in counters (square mouthpiece), and open to increase airflow as inhaler resistance is higher, such as with Proventil HFA inhalers with the yellow 3M boot. The valve 222 is made from an elastomeric material such as silicone or TPE. In one embodiment, the valve 222 is located on the backpiece 114 to promote airflow through the chamber, helping to evacuate the suspended medication into the patient's lungs. In this way, the variable opening size is defined by the one or more one-way inhalation valves 222 disposed over one or more inlets 220.

During operation the user 148 holds the chamber in the horizontal position, such that gravity does not play an unintended role in the movement, or resistance thereto, of the turbine 170. To prevent inadvertent movement of the turbine, the dip 182 in the track prevents the turbine 170 from rolling due to inadvertent tilting of the chamber during setup for example at an angle α, as shown in FIGS. 9 and 10, which may be between and including 0 and 20 degrees. The dip 182 is positioned adjacent the dosage indicator 160, for example underlying or immediately downstream of the dosage indicator 160 when the dosage indicator is positioned in the pre-inhalation position. The dip 182 may be designed as a concave curvature in the track, channel and rack. In this embodiment, the channel and track are curvilinear. Even with the dip, the entirety of the track lies in the same plane, defined for example by the X and Y directions. The system is calibrated such that any gravity that must be overcome by the turbine 170 climbing out the dip 182 is incorporated into the overall design such that the turbine reaches the complete dosage position when the medication is fully administered.

In other embodiments, the flow channel and track may not be linear, but rather follow a curved or curvilinear path, for example a circular path, which may lie in the horizontal plane for example. For example, the flow indicator may follow a circular path wherein the pre-inhalation and compete dosage positions are adjacent.

Tidal volumes and max inhalation rates vary between different age groups, where infants have the lowest and adults the highest. Ideally the turbine 170 would have a high sensitivity to inhalation (<7 L/min) for all age groups, however, high sensitivity may cause the turbine to move to the distal end of the channel, or complete dosage position, too quickly since the length of the channel may be limited, for example if integrally formed with the holding chamber. In one embodiment, the adult turbine flow channel 150 may be much longer (~2-3×) so as to be able to detect very low inhalation rates (<7 L/min), assuming the resistance due to the channel length increase was not too high. By varying the turbine sensitivity, the turbine 170 may be optimized to work for the correct inhalation volumes of the three different patient groups. The turbine's weight may be reduced for high sensitivity. For example, in one embodiment, the turbine blades 186 may be thinned, and the diameter of the fins is reduced. Overall, a lower moment of inertia is desired for high sensitivity. Turbine blade diameters above 12 mm may become less sensitive as the fins require more material and less weight.

The turbine movement is highly sensitive to airflow since the turbine is very light, but also there is minimal friction restricting the movement of the turbine, as the rack 206 and pinion 188 design forces the turbine 170 to roll at a fixed rotation to distance rate. In other embodiments, the dosage indicator may slide in the track, with attendant friction providing resistance.

Figure 12:
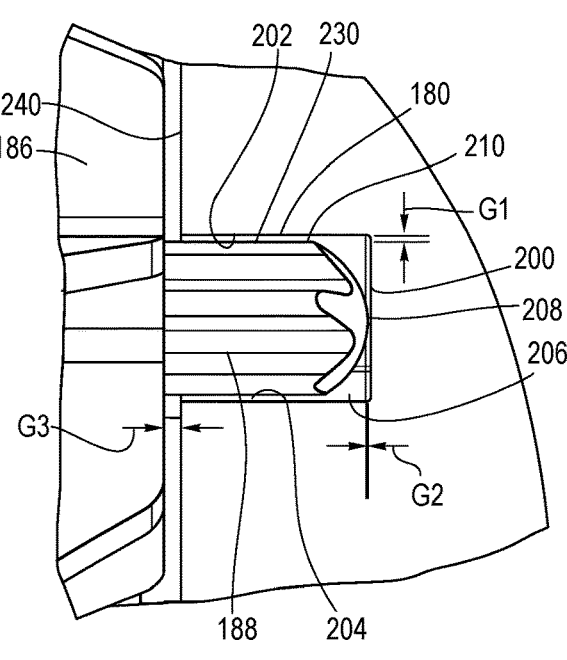
FIG. 12 is an enlarged partial view of a portion of a dose indicator disposed in a track.
Figures 13, 14, 15, 16:
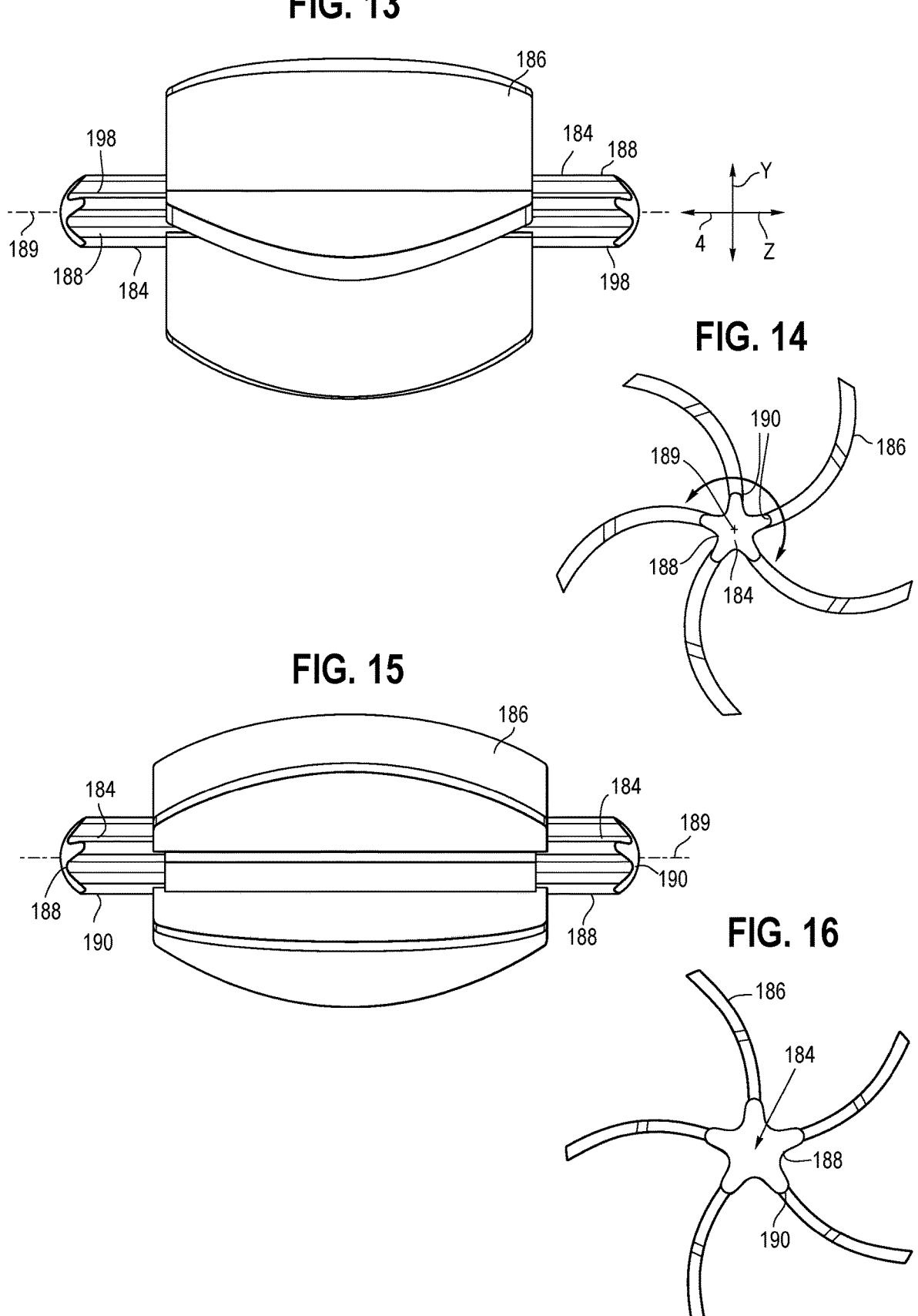
FIG. 13 is a front view of one embodiment of a dose indicator.
FIG. 14 is an end view of the dose indicator shown in FIG. 13.
FIG. 15 is a front view of another embodiment of a dose indicator.
FIG. 16 is an end view of the dose indicator shown in FIG. 15.
Figure 17:
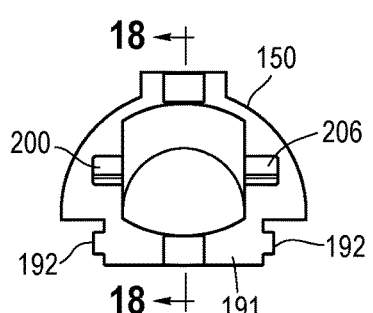
FIG. 17 is an end view of one embodiment of a flow channel.
Figure 19:
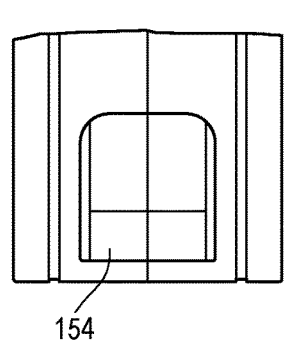
FIG. 19 is a partial, bottom view of the flow channel shown in FIG. 18.
Figure 18:
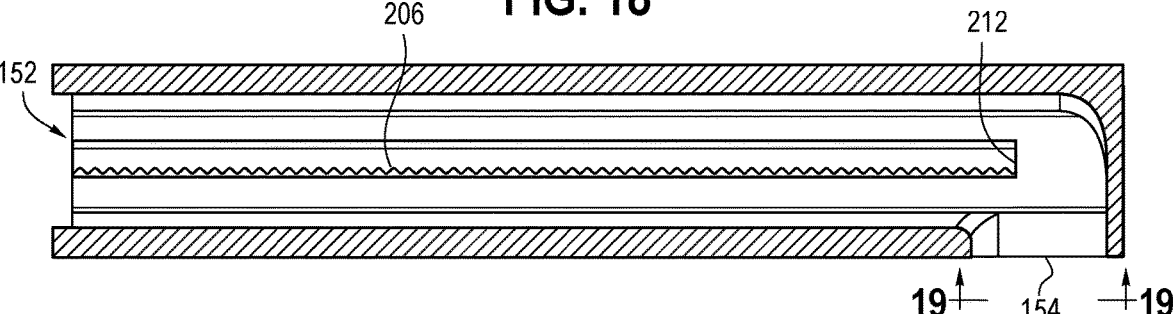
FIG. 18 is a cross-sectional view of the flow channel taken along line 18-18 in FIG. 17.
Figure 20:
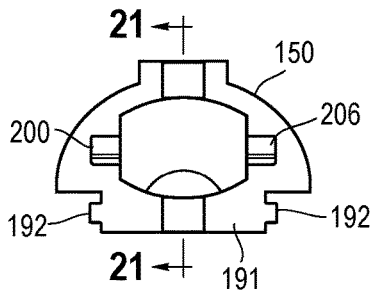
FIG. 20 is an end view of another embodiment of a flow channel.
Figure 22:
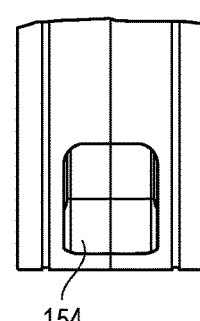
FIG. 22 is a partial, bottom view of the flow channel shown in FIG. 21.
Figure 21:
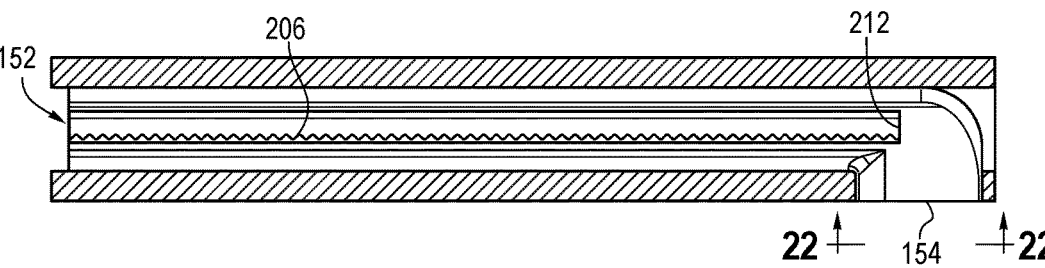
FIG. 21 is a cross-sectional view of the flow channel taken along line 18-18 in FIG. 17.

Air passing through the flow channel from the inlet 152 to the outlet 154 causes the turbine 170 to rotate and translate in the flow channel 150. Because the turbine 170 is contacting the channel via the pinion 188, the turbine travels along the channel at a much lower speed than the linear speed of the tip of the blade 186 of the turbine. In one embodiment a smaller diameter pinion 188 causes the turbine to spin more times to travel the distance of the channel, therefore allowing design control of the turbine response. As shown in FIG. 12, a gap (G1) or clearance, which is less than the depth of the teeth 190, 207 of the pinion and/or rack, is provided between the outer circumferential surface 230, or top, of the pinion gear and the upper surface 202 of the track, or slot. This clearance or gap (G1) ensures that the turbine pinion 188 remains engaged with the rack 206 during use and transport, but avoids any frictional engagement between the pinion gear 188 and the upper surface 202 of the track. To prevent the turbine blades 186 from hitting the side wall 240 of the channel and binding, the gap (G2) between the ends of the shaft and the side walls of the track is smaller than the gap (G3) between the channel side wall 240 and the turbine blades 186.

A primary source of drug delivery feedback is by the user observing, for example visually observing or seeing the turbine 170 move to the end of the track or flow channel 150 and stop. The turbine 170 may be made from a colored (non-clear or white) plastic (e.g., black, red, green, orange, blue, etc.) to provide contrast to the user, so their eyes do not need to focus on the turbine features, but rather see the different color object. The turbine material may be mixed with a glow in the dark additive, or a glow in the dark coating may be applied, so that the caregiver or user can see the turbine 170 move when administering medications in the dark.

Another source of feedback comes from the sound that the turbine 170 makes as it moves along the flow channel 150 due to the pinion teeth 190 rolling over the teeth 207 of the rack. In this way, observing the translation of the dosage indicator 160 includes listening to the translation of the dosage indicator in the flow channel as the dosage indicator rotates. As such, the term "observing" refers to seeing or listening. The sound will indicate to the user if the turbine is moving, since it makes a subtle rattling sound. In addition, when the turbine hits the end of the channel, engaging for example the stop 212, and thereby reaches the complete dosage position, the turbine 170 provides a different audible queue to the user/caregiver indicative of the position being reached.

In one embodiment, the dosage indicator assembly incudes a plurality (shown as four) of components, each of which may be injection molded: the turbine 170, a flow channel top/cover 260, a channel base 262 and a front cover 264. The channel top/cover and bottom/base may be coupled, for example by snap or sliding fit/interface and/or with adhesive. Each of the top and bottom includes a horizontal wall defining one of the upper and lower surfaces 202, 204 of the track. In another embodiment, the flow channel part may include a pair of side components. The base component defines the bottom half of the channel, including the track and rack teeth. The base component may be made separate from or integral with the chamber body. If separate, the base component may be coupled to the chamber body with insert portions/guide, tabs, adhesive or other fasteners. Once assembled, the cover and base define the channel.

After the turbine 170 is disposed in the channel, a front cover 264 may positioned over and secured to the front of the flow channel to prevent the turbine 170 from falling out. The front cover 264 may have holes to allow air flow into the turbine channel and define the inlet 152. The front cover may be made from a variety of materials, such as metal or plastic screen. In this way, the front cover maintains the turbine 170 in the flow channel such that the turbine does not pose a choking hazard. The flow channel 150 may be detachable from the chamber body so the chamber body may be easily cleaned. The flow channel has an outlet 154 which is mated/communicates with and overlies the inlet 156 in communication with the holding chamber.

The channel assembly, and the top cover in particular, may be made from a transparent or translucent material, like polypropylene (PP) plastic (or possibly other polyolefins, nylons, MABS, polycarbonate), so that the user may see the turbine move along the length of the flow channel. As mentioned, the turbine 170 may be a contrasting color (e.g., black or a vibrant color) relative to the color of the holding chamber and flow channel. The turbine sensitivity is dependent on weight, therefore a lightweight plastic like PP may allow the turbine to be more sensitive than if it were made from a higher density plastic such as PET.

The turbine 170 includes the shaft 184, configured with a pair of pinion gears 188 at opposite ends thereof, that defines a laterally extending rotation axis 189, which is perpendicular to the longitudinally extending flow channel and track. The plurality of branching fin blades 186, extend radially outwardly from the shaft 184 and are arranged in a Savonius, or drag, design (ex, straight fins, helical fins, cup design). In one embodiment, the turbine 170 is configured with five blades 186. Other embodiments may be configured with or between 3 and 8 blades.

The effective turbine diameter (distance across/between the tips of the fins when viewed along the axis of the turbine, or the diameter of the space filled by the rotating turbine) is 8.6 mm 7.2 mm and 6.6 mm, for adult, child and infant turbines, respectively, but may be varied by 1-2 mm each. The turbine diameter dictates the length of the blades/fins, which impacts the turbine weight and therefore sensitivity to airflow. The weight of the adult, child and infant turbines may be 0.077 g, 0.046 g, and 0.033 g, respectively, but may be up to and including 0.125 g, for example as being suitable for adults. The turbine blade/fin thickness may be varied to increase or decrease the weight of the turbine, therefore influencing the sensitivity of the turbine. The adult or infant blade/fin thickness may be between 0.1 mm and 0.6 mm. In various embodiments, the thickness of the blades/fins for adults is 0.35 mm, 0.25 mm for children and 0.20 mm for infants. For the adult, child and infant design, the blades/fins may have a curvature radius between 2 mm and 6.5 mm, with 2.5 mm being suitable.

The shaft 184 extends past the length of the blades 186 and is formed in the shape of the pinion 188. The preferred length of the shaft or pinion is around 2.5 mm, which may be selected based on a balance of added weight and friction as turbine length increases. The length of the pinions may be between and including 0.5 mm and 5 mm.

The pinion 188 may have various number of teeth 190, for example between 4 and 7 teeth, with 5 teeth being suitable in one embodiment. More teeth may help prevent the turbine from popping out of the tracks. The pinion diameter, or outer circumferential periphery of the pinion gear 188 and teeth 190, may be between and including 0.5 mm to 2.5 mm, with various embodiments having a diameter of between and including 1 mm and 1.75 mm, which offers a suitable ratio between the outer fin diameter and the pinion diameter. In one embodiment, the pinion gear has a 1.75 mm.

The profile of the outer surface 276 of the flow channel may be rounded for aesthetics and to improve the tactile feel and cleanability. To maximize space within the curved channel, the turbine 170 has a rounded profile when viewed perpendicular to the turbine axis, maintaining a uniform clearance from the channel. The length of the flow channel 150 and cross-sectional shape are shaped to conform to the shape of the turbine, while leaving a 0.5 mm gap between the blades and the interior surface of the flow channel 150 to prevent contact. The opening 152, or inlet that connects the channel to the chamber minimizes the resistance of air flow between the channel and the chamber. In one embodiment, the opening 152 is 10 mm by 9 mm, but the opening may be smaller or larger.

During operation, the method of dispensing the medication includes disposing an aerosolized dose of medicament in an interior volume 110 of a chamber housing, for example by actuation the inhaler 106, which release a predetermined, metered dosage of medicament. The medication may be dispensed into the holding chamber while the interface is engaged with the patient, or beforehand. The method further includes inhaling through the user interface 104 coupled to the chamber housing and thereby withdrawing the aerosolized dose of medicament from the interior volume, translating the dosage indicator 160 in the flow channel 150 in fluid communication with the chamber housing from the pre-inhalation position to the completed dosage position as shown in FIGS. 7A-C, observing the translation of the dosage indicator 160, and ceasing inhaling when the dosage indicator 160 reaches the complete dosage position. Air is entrained into the holding chamber as the medication is inhaled by air flow from one or more of the inlets, depending on the resistance and size of the variable size opening. Translating the dosage indicator includes rotating the turbine in one embodiment. Proper inhaler drug delivery through a holding chamber 102 may require an adult to inhale 500 mL, children to inhale 300 mL and infants to inhale 50 mL. The breath tracker system approximates inhalation rate to inhalation volume.

The flow rate at which the turbine 170 is designed to begin moving is called the "trigger flow rate". This flow rate for adults could be between 5-30 L/min, 5-20 L/min for children and 5-10 L/min for infants, but ideally at 15 L/min, 10 L/min and 5 L/min respectively. The weight, pinion diameter, channel length, channel cross-sectional area, backpiece valved hole size and other various features may impact the turbine's trigger flow rate. In one embodiment, the holding chamber has three inlets: through the channel, the inhaler/receptacle and the valve. For each of the age variant designs (adult, child, and infant), the turbine and channel is designed to begin moving at a given pressure based on the average tidal breath flow rates.

Figure 23A:
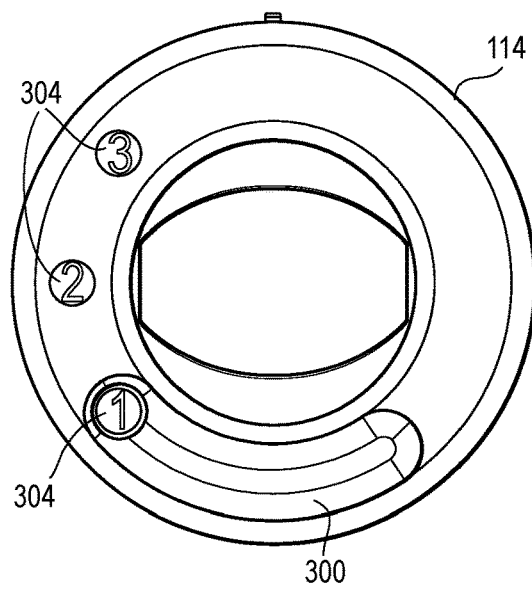
FIGS. 23A-C are end views of one embodiment of a backpiece adapter with a variable size opening providing three different inlet sizes.
Figure 23B:
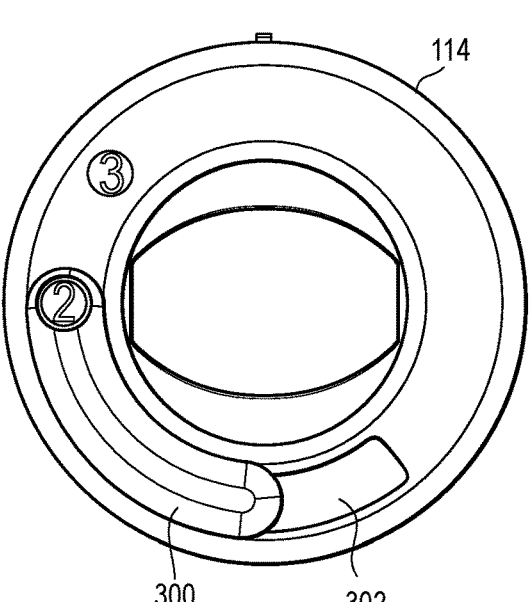
Figure 23C:
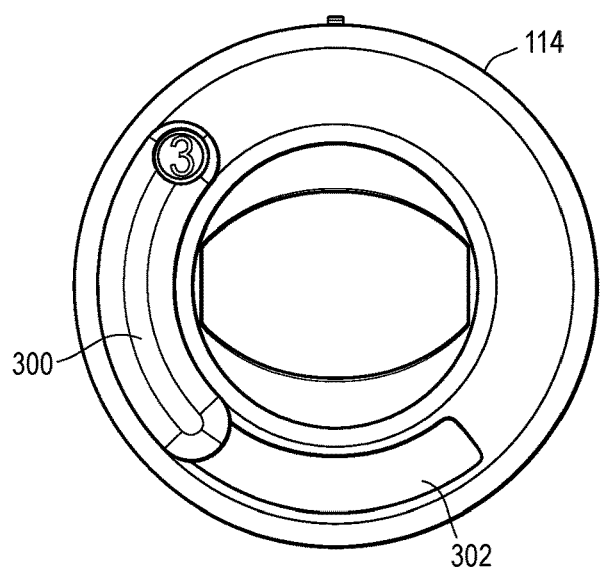

In an alternative embodiment, a sliding dial 300 aligns with various dial numbers, or indicators 304, to vary the size of an opening 302 defining an inlet in the backpiece 114. For example, the indicators may be configured as alphanumeric characters, such as letters, numbers and/or as other shapes or symbols, which may be identified by different colors. Before use, the user aligns the dial 300 with the corresponding inhaler setting, using the indicators 304. The inhaler setting may be listed on the inhalation device, instructions accompanying the device or inhaler, as well as online. At the trigger flow for adults, the dial opening 302, or inlet 220, has an isolated flow rate of 12 L/min at setting 3 (max setting, fully open), and a flow rate of 8 L/min at setting 2 (mid setting, partially open) and 0 L/min at setting 1. While the embodiment shown in FIGS. 23A-C is configured with three settings; more settings may provide more resolution and improved breath tracker accuracy. Other embodiments may have between and including two and twenty settings, or between and including five and ten settings.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A medication delivery system comprising:
a chamber housing defining an interior volume and comprising an inlet adapted to receive a dosage of medicament and an outlet spaced apart from the inlet, wherein the inlet and outlet are in fluid communication with the interior volume;
a flow channel in fluid communication with the interior volume; and
a dosage indicator translatable in the flow channel from a pre-inhalation position to a complete dosage position, wherein a positioning of the dosage indicator in the complete dosage position indicates a complete administration of the dosage of medicament through the outlet, wherein the dosage indicator is visible through the flow channel as the dosage indicator is translated between the pre-inhalation position and the complete dosage position;

wherein the dosage indicator comprises a turbine, wherein the turbine is rotatable as the turbine is translated from the pre-inhalation position to the complete dosage position.

2. The medication delivery system of claim 1 wherein the dosage indicator is translatable along a linear path between the pre-inhalation position and the complete dosage position.

3. The medication delivery system of claim 1 further comprising a user interface coupled to the chamber housing, wherein the dosage indicator is closer to the user interface in the pre-inhalation position than in the complete dosage position.

4. The medication delivery system of claim 1 wherein the inlet and outlet are spaced apart in a longitudinal direction, wherein the flow channel extends in the longitudinal direction, wherein the turbine is rotatable about a rotation axis extending transverse to the longitudinal direction, and wherein the rotation axis is translatable in the longitudinal direction.

5. The medication delivery system of claim 1 further comprising an auditory indicator adapted to provide an audible signal when the dosage indicator is translated to the complete dosage position.

6. The medication delivery system of claim 5 wherein the dosage indicator is the auditory indicator.

7. The medication delivery system of claim 1 wherein the flow channel comprises a track, wherein the turbine is moveable along the track between the pre-inhalation position and the complete dosage position.

8. The medication delivery system of claim 7 wherein the track comprises a rack, and wherein the turbine comprises a pinion gear rotatably engaging the rack.

9. The medication delivery system of claim 7 wherein the track comprises a dip adjacent the dosage indicator when positioned in the pre-inhalation position.

10. The medication delivery system of claim 1 further comprising an adaptor coupled to the chamber housing, wherein the inlet comprises a first inlet defined by the adapter, and wherein the adapter further comprises a second inlet communicating with the interior volume, the second inlet comprising a variable size opening.

11. The medication delivery system of claim 10 wherein the variable size opening is defined by a one-way inhalation valve disposed over the second inlet.

12. The medication delivery system of claim 10 wherein the variable size opening is defined by a dial moveable relative to the second inlet.

13. The medication delivery system of claim 10 wherein the flow channel is in fluid communication with the interior volume at a third inlet spaced apart from the first and second inlets.

14. The medication delivery system of claim 10 wherein the flow channel is in fluid communication with the interior volume at a third inlet spaced apart from the first and second inlets.

15. A medication delivery system comprising:
a chamber housing defining an interior volume and comprising an inlet adapted to receive a dosage of medicament and a user interface spaced apart from the inlet in a longitudinal direction, wherein the inlet and the user interface are in fluid communication with the interior volume;
a flow channel in fluid communication with the interior volume and extending in the longitudinal direction; and
a dosage indicator translatable in the flow channel from a pre-inhalation position proximate the user interface to a complete dosage position proximate the inlet, wherein a positioning of the dosage indicator in the complete dosage position indicates a complete administration of the dosage of medicament through the user interface, wherein the dosage indicator comprises a turbine that is rotatable in, and visible through, the flow channel as the dosage indicator is translated between the pre-inhalation position and the complete dosage position.

16. The medication delivery system of claim 15 wherein the dosage indicator is translatable along a linear path between the pre-inhalation position and the complete dosage position.

17. The medication delivery system of claim 15 further comprising an auditory indicator adapted to provide an audible signal when the dosage indicator is translated to the complete dosage position.

18. The medication delivery system of claim 17 wherein the turbine is the auditory indicator.

19. The medication delivery system of claim 15 wherein the flow channel comprises a track, wherein the turbine is translatable along, and rotatable on, the track between the pre-inhalation position and the complete dosage position.

20. The medication delivery system of claim 19 wherein the track comprises a rack, and wherein the turbine comprises a pinion gear rotatably engaging the rack.

21. The medication delivery system of claim 19 wherein the track comprises a dip adjacent the dosage indicator when positioned in the pre-inhalation position.

22. The medication delivery system of claim 15 further comprising an adaptor coupled to the chamber housing, wherein the inlet comprises a first inlet defined by the adapter, and wherein the adapter further comprises a second inlet communicating with the interior volume, the second inlet comprising a variable size opening.

23. The medication delivery system of claim 22 wherein the variable size opening is defined by a one-way inhalation valve disposed over the second inlet.

24. The medication delivery system of claim 22 wherein the variable size opening is defined by a dial moveable relative to the second inlet.

* * * * *